United States Patent [19]

Scharpf

[11] 4,081,488
[45] Mar. 28, 1978

[54] PROCESS FOR PREPARING 1,1-DIHALO-4-METHYL-1,3-PENTADIENES

[75] Inventor: William George Scharpf, Yardley, Pa.

[73] Assignee: FMC Corporation, Philadelphia, Pa.

[21] Appl. No.: 644,277

[22] Filed: Dec. 24, 1975

[51] Int. Cl. .............................................. C07C 11/16
[52] U.S. Cl. ................................ 260/654 R; 260/633; 560/124
[58] Field of Search ................. 260/468 T, 654 R, 633

[56] References Cited

U.S. PATENT DOCUMENTS

| | | | |
|---|---|---|---|
| 2,594,184 | 4/1952 | Ladd | 260/633 |
| 2,636,057 | 4/1953 | Cutcher | 260/682 |
| 3,009,946 | 11/1961 | Takei | 260/468 H |
| 3,244,766 | 4/1966 | Keough | 260/682 |

FOREIGN PATENT DOCUMENTS

| | | | |
|---|---|---|---|
| 800,006 | 9/1973 | Belgium. | |
| 975,383 | 9/1975 | Canada. | |
| 313,426 | 6/1929 | United Kingdom | 260/482 |
| 576,480 | 4/1946 | United Kingdom | 260/482 |

OTHER PUBLICATIONS

Atavin, J. Org. Chem., USSR, 9, 320 (1973).
Corothers, J. Amer. Chem. Soc., 46, 1675 (1924).
Catch, J. Chem. Soc., 278, (1948).
Colonge, Bull. Soc. Chem. Fr., 204 (1957).
Elliott I, Nature, 244, 456 (1973).
Elliott II, Nature, 246, 169 (1973).
Julia, Bull. Soc. Chem. Fr., 1828 (1959).
Kent, Organic Synthesis, vol. III, 490-492 (1955).
Koozman, Rec. Trav. Chim Pays-Bos, 77, 923 (1958).
Pochat, Bull. Soc. Chim. Fr., 3846 (1972).
Royals, Advanced Organic Chemistry, 708-717 (1954).
Sanders, Chem. & Eng. News, 19 (7/28/75).
Satchell, Quart. Rev., 17, 160 (1963).
Schmerling, J. Amer. Chem. Soc., 71, 701 (1949).
Soulen, J. Org. Chem., 32, 2661 (1967).
Tuley, J. Amer. Chem. Soc., 47, 3061 (1925).
Wilds, Organic Reactions, vol. II, pp. 178-223 (1944).
Heilbron, J. Chem. Soc. 1430 (1949).
Zakhaikin, Izv. Okad. Nauk, SSSR, Ser. Khim, 313 (1956).
Farkas, Collect. Czech. Chem. Comm., 24, 2230 (1959).
Royals, Advanced Organic Chemistry, pp. 230-233 (1954).
Sultauov, Chem. Abst., 56:2917d (1962).
Bulatova, Chem. Abst., 53:193b (1959).
Wagner, "Synthetic Organic Chemistry," pp. 32-35 & 149-152, (1953).
Komarov, Chem. Abst. 68:63019n (1967).
Bader, Aldrichimica Acta, vol. 9, pp. 49-51 (1976).

*Primary Examiner*—James O. Thomas, Jr.
*Assistant Examiner*—Michael Shippen
*Attorney, Agent, or Firm*—Richard L. Hansen; Henry R. Ertelt

[57] ABSTRACT

1,1-Dihalo-4-methyl-1,3-pentadienes, key intermediates in the syntehsis of insecticidal dihalovinylcyclopropanecarboxylates, may be prepared in three steps beginning with the Friedel Crafts condensation of a vinylidene halide and an isobutyryl halide in the presence of a Lewis acid catalyst, followed by reduction of the 1,1-dihalo-4-methyl-1-penten-3-one produced thereby, and dehydration of the resulting 1,1-dihalo-3-hydroxy-4-methyl-1-pentene.

3 Claims, No Drawings

PROCESS FOR PREPARING 1,1-DIHALO-4-METHYL-1,3-PENTADIENES

BACKGROUND OF THE INVENTION

1. Field of the Invention

This invention relates to a new and improved chemical process for preparing 1,1-dihalo-4-methyl-1,3-pentadienes, key intermediates in a known method for the production of certain pyrethriod insecticides, and to new compositions of matter useful in the practice of the chemical process.

2. Description of the Prior Art

Pyrethriods, naturally-occurring and synthetic derivatives of cyclopropanecarboxylic acid, have long been of interest as insecticides because they are active against a wide range of insect species, they display relatively low toxicity toward mammals, and they do not leave harmful residues. A notable recent technical advance in the pyrethroid art was the discovery of dihalovinylcyclopropanecarboxylates; for example, 3-phenoxybenzyl 2-($\beta,\beta$-dihalovinyl)-3,3-dimethylcyclopropanecarboxylates, having an outstanding combination of insecticidal properties [Elliott et al., Nature, 244,456(1973); ibid., 246, 169(1973); Belgian Pat. No. 800,006]. Since Elliott's discovery, a great deal of interest has been generated worldwide in economical processes for the production of this type of pyrethroid.

Several years before Elliott's discovery, a method for synthesizing ethyl 2-($\beta,\beta$-dichlorovinyl)-3,3-dimethylcyclopropanecarboxylate was reported [Farkas et al., Coll. Czech. Chem. Comm., 24, 2230(1959)]. The ethyl ester of Farkas leads to an Elliott pyrethroid by subsequent reaction with 3-phenoxybenzyl alcohol [Nature, 244,456(1973)]. According to the first step of the Farkas method, chloral may be condensed with either isobutenyl magnesium bromide or with isobutylene, using a free radical catalyst with the latter, to produce pentenols which then may be reacted as follows, yielding the cyclopropanecarboxylate in four additional steps:

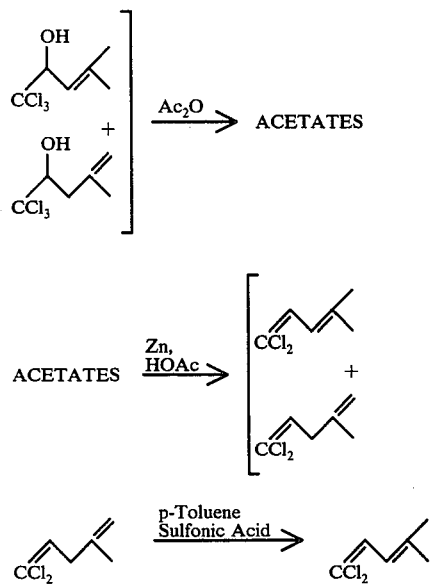

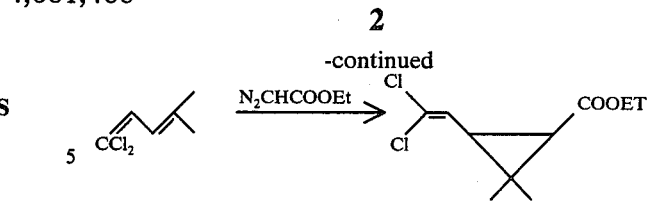

However, the overall conversion of readily available isobutylene to 1,1-dichloro-4-methyl-1,3-pentadiene, the key reactant in the fourth, ring-closing step of the Farkas method is reportedly less than 40%. Furthermore, for every kilogram of dichloropentadiene produced in the fourth step, more than a kilogram of zinc dust is consumed in the third step. In a recent year, U.S. producers alone sold about 300 million kilograms of synthetic organic insecticides [Chemical and Engineering News, July 28, 1975, p. 19]. If the Elliott pyrethroid becomes a major agricultural commodity, commercial production of this key intermediate by the Farkas method would seriously tax the world supply of zinc. Thus, other more practical and economical processes capable of yielding 1,1-dichloro-4-methyl-1,3-pentadiene from readily available starting materials have been sought.

SUMMARY OF THE INVENTION

It has now been found that the aforesaid disadvantages inherent in the Farkas route can be avoided in a novel, improved, three-step chemical process for preparing a 1,1-dihalo-4-methyl-1,3-pentadiene. According to the process of this invention, a vinylidene halide is first condensed with an isobutyryl halide in the presence of a Lewis acid to produce a 1,1-dihalo-4-methyl-1-penten-3-one, which subsequently is reduced to the corresponding secondary alcohol, and then dehydrated, yielding the desired 1,1-dihalo-4-methyl-1,3-pentadiene.

In addition to avoiding the aforesaid disadvantages of the Farkas route, the process of this invention utilizes ionic reactions, minimizing the spectrum of by-products often obtained in a free radical reaction, such as, for example, in the free radical reaction between chloral and isobutylene to produce the mixture of pentenols in the first step of the Farkas process. Thus, this invention produces a higher yield of the desired product. The reactants and intermediates of this invention may be transferred readily and processed in conventional chemical manufacturing equipment. In the Farkas process beginning with the condensation of chloral and isobutylene, a gaseous reactant must be handled, necessitating extensive capital outlays for special cooling equipment when the reaction is conducted on a commercial scale.

The three-step process of this invention is represented by the following chemical equations, wherein X represents a halogen atom; each reaction depicted is discussed in detail below:

STEP 1

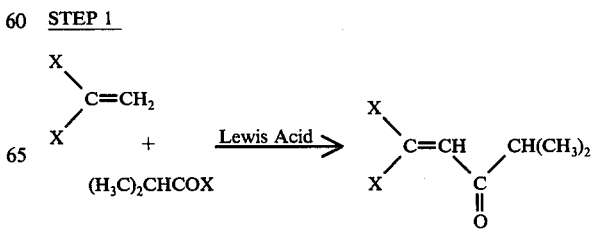

STEP 2

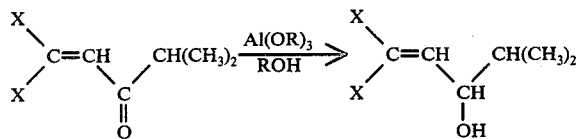

STEP 3

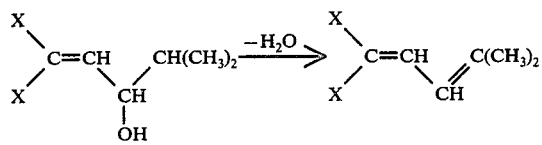

DETAILED DESCRIPTION OF THE INVENTION

STEP 1

In Step 1, a vinylidene halide (1,1-dihaloethene) is condensed with an isobutyryl halide (2-methylpropanoyl halide) in the presence of a Lewis acid to produce a 1,1-dihalo-4-methyl-1-penten-3-one. Each of the halogen atoms of the vinylidene halide may be fluorine, chlorine or bromine; the isobutyryl halide may be either a chloride, or bromide. In order to produce a 1,1-dihalo-4-methyl-1-penten-3-one in which the two halogen atoms are the same, it is preferable if all three of the halogen atoms in these reactants are identical. If all three halogen atoms are not identical, a 1,1-dihalo-4-methyl-1-penten-3-one having two different halogen atoms may result. For example, 1-bromo-1-chloro-4-methyl-1-penten-3-one may be prepared by reacting vinylidene bromide with isobutyryl chloride.

1,1-Dichloro-4-methyl-1-penten-3-one may be prepared by condensing vinylidene chloride and isobutyryl chloride. The monomer, vinylidene chloride, is readily available in commerce. Isobutyryl chloride may be prepared conveniently from isobutyric acid. [See R. E. Kent and S. L. McElvain, Organic Synthesis Collective Volume III, John Wiley and Sons, Inc., New York, N.Y., 1955, page 490].

The condensation of vinylidene chloride with alkanoyl chlorides in the presence of the Lewis acid, aluminum chloride, to produce $\beta,\beta$-dichlorovinyl ketones was developed by Heilbron, et al. [J. Chem. Soc., 1430 (1949)], who condensed acetyl chloride with vinylidene chloride to produce methyl $\beta,\beta$-dichlorovinyl ketone, separating the product by steam distilling a carbon tetrachloride extract of the reaction mixture, followed by fractionally distilling the organic phase of the steam distillate.

Soulen et al. first made 1,1-dichloro-4-methyl-1-penten-3-one [R. L. Soulen, D. G. Kundiger, S. Searles and R. A. Sanchez, J. Org. Chem., 32, 2661 (1967)], utilizing the basic Heilbron process, but conducting the reaction in a solvent ($CCl_4$).

In 1973, Atavin and his colleagues reported the preparation of a number of alkyl and aryl $\beta,\beta$-dichlorovinyl ketones. These workers discovered that the hydrolysis of labile $\beta,\beta$-dichlorovinyl ketones could be avoided and yields increased by treating the reaction mixture with potassium carbonate, avoiding the steam distillation [A. S. Atavin, G. G. Levkovskaya and A. N. Mirskova, J. Org. Chem. (USSR), 9, 320 (1973)]. They also employed a mixture of the Lewis acids, ferric chloride and aluminum chloride, in one variation of their synthesis.

In preparing a 1,1-dihalo-4-methyl-1-penten-3-one, according to Step 1 of this invention a solvent is not required, but it is convenient to employ a solvent in which to dissolve the reactants; the reaction is then easier to control, and neither reactant is wasted. Various solvents, such as carbon tetrachloride, chloroform, or methylene chloride, may be employed. The reaction may also employ an excess of one of the reactants as a solvent; for example, isobutyryl chloride.

The concentration of the reactants in the solvent can vary over a wide range, but at low concentrations, the reaction is too slow. At high concentrations, the reaction is difficult to control. Satisfactory results are obtained at reactant concentrations in the range of about 1 to 10 molar, preferably about 2 to 5 molar.

Step 1 requires a Lewis acid catalyst. A number of different catalysts in this class are suitable, such as ferric chloride, aluminum chloride, zinc chloride, zinc bromide, boron trifluoride, and the like. Aluminum chloride is readily available in commerce and is ordinarily preferred for that reason. Although the result of the reaction is not critically dependent upon the ratio of the Lewis acid to the other reactants, approximately equimolar quantities give good results.

According to the stoichiometry, the molar ratio between the vinylidene halide and the isobutyryl halide should be 1.0. However, it is desirable to employ one of the reactants in up to about 5% excess so as to drive the reaction to completion.

In order to ensure an optimum yield and to avoid the formation of undesirable by-products, it is necessary to control the temperature. The reaction medium should be cooled to a temperature of about 0° C. while the reactants are mixed. After the reactants have been mixed, it is permissible to allow the temperature to rise.

The product may be separated by steam distillation, but the yield is improved if the reaction mixture is treated with aqueous sodium or potassium carbonate as taught by Atavin, et al. [J. Org. Chem. (USSR), 9, 320 (1973)].

Step 1 of this process will be understood more readily by reference to Example I.

In the Examples which follow, temperatures are in degrees centigrade. Where ir spectra are given, only the frequencies of the most prominent absorption maxima appear. Tetramethylsilane was employed as an internal standard for the nmr spectra. In reporting the nmr data, the abbreviations have the following significance: s, singlet; d, doublet; t, triplet; q, quartet; m, multiplet. Any of these abbreviations may be preceded by b for broad or d for double, for example, d.d., double doublet; b.t., broad triplet. Vapor phase chromatographic analyses were performed by employing a 48 in. × ⅛ in. diameter column packed with a silicone suspended in diatomaceous earth. The injection port temperature was 275°. The helium flow rate was 30 ml/min. The instrument was programmed to hold the initial column temperature of 100° for 9 min. after injection, after which the column temperature rose 10°/min. to 200°. The thermal conductivity temperature was 300°.

EXAMPLE I

Preparation of 1,1-Dichloro-4-methyl-1-penten-3-one

A. Using Aluminum Chloride

1. Steam Distillation of the Reaction Mixture

A solution of 89 gm (0.835 mole) of isobutyryl chloride in 250 ml of carbon tetrachloride was cooled to between −10° and −20°. With stirring, 112 gm (0.840 mole) of anhydrous aluminum chloride was added slowly. To the resultant stirred mixture, 85 gm (0.876 mole) of vinylidene chloride was added dropwise while cooling the reaction mixture to −10°. The stirred reaction mixture was then allowed to warm to room temperature over a 2 hour period, at the end of which it was poured into a mixture of hydrochloric acid and ice. The organic layer was separated, and the aqueous layer was extracted with two 150-ml portions of carbon tetrachloride. The extracts and the organic layer were combined and fractionally steam distilled.

The fractions with boiling points of 60°–100° were combined. The organic layer was separated and dried over magnesium sulfate. The solution was filtered, and the solvent was evaporated under vacuum. The residue was then vacuum distilled to yield 63.2 gm (42% yield) of crude 1,1-dichloro-4-methyl-1-penten-3-one; b.p., 60°–81°/14mm. The ir spectrum of the distillate was consistent with the assigned structure.

2. Treatment of the Reaction Mixture with Sodium Carbonate

To a solution of 1773 gm (16.63 moles) of isobutyryl chloride in 5.5 liters of anhydrous carbon tetrachloride at −2° was added 2165 gm (16.21 moles) of aluminum chloride. The temperature rose to 10°. The reaction mixture was recooled to −2°, and 1900 gm (19.59 moles) of vinylidene chloride was added dropwise. Upon complete addition, the reaction mixture was allowed to warm to room temperature over a period of 2.5 hours. The reaction mixture was then heated to 40°–50° for ½ hour and poured over crushed ice. The mixture was allowed to stand for 16 hours, separated, and then the carbon tetrachloride layer was washed with water.

The aqueous layer was extracted three times with carbon tetrachloride. The organic layers were combined, washed again with water, and separated. The organic layer was then washed with a 10% aqueous solution of sodium carbonate (1000 ml of aqueous solution to 3500 ml of organic layer). One wash was sufficient to neutralize the acid. The organic layer was finally washed with water, and filtered through magnesium sulfate. The carbon tetrachloride was removed by distillation. The residue was distilled under reduced pressure from the same vessel to give 1780 gm (65.6% yield) of 1,1-dichloro-4-methyl-1-penten-3-one; b.p., 74°–76°/13mm [Soulen, et al., op. cit., report 74°–78°/14mm].

B. Using a Mixture of Aluminum Chloride and Ferric Chloride

A solution of 100 gm (0.939 mole) of isobutyryl chloride in 380 ml of carbon tetrachloride was cooled to −10°. With vigorous stirring, a mixture of 142.4 gm (1.068 moles) of anhydrous aluminum chloride and 1.2 gm (0.074 moles) of anhydrous ferric chloride was added under a nitrogen atmosphere. The reaction mixture was maintained at −10° to −20° as 125.6 gm (1.296 moles) of vinylidine chloride was added over ½ hour. Upon complete addition, the vigorously stirred reaction mixture was allowed to warm to room temperature over a 3 hour period. The mixture was then heated rapidly to 58°, cooled, and poured into crushed ice. The aqueous and organic layers were separated. The aqueous layer was extracted twice with carbon tetrachloride. The organic layers were combined and washed with water, then thrice with an aqueous solution of 10% sodium carbonate, then once with water. The organic phase was heated under atmospheric pressure to remove most of the solvent.

The residue was distilled under reduced pressure to give 67.2 gm of 1,1-dichloro-4-methyl-1-penten-3-one; b.p., 69°/9.0–9.4mm.

C. Using Ferric Chloride

To a solution of 53.5 gm (0.5 mole) of isobutyryl chloride and 45 gm (0.27 mole) of ferric chloride in 50 ml of methylene chloride cooled to 50°, and maintained below 10°, was added, with stirring, 53.2 gm (0.55 mole) of vinylidene chloride over a 1 hour period. After the addition, the reaction mixture was allowed to warm to room temperature for 3 hours before being poured over 100 gm of crushed ice. The layers were separated, and the organic solution was washed three times with 50-ml portions of water before being dried over magnesium sulfate. After being filtered, the solution was diluted with 50 ml of methylene chloride. The diluted solution was washed twice with dilute aqueous potassium carbonate and then with water before being distilled under reduced pressure, yielding 1.4 gm of crude 1,1-dichloro-4-methyl-1-penten-3-one; b.p., 41°–62°/4.1–4.7mm. The presence of the dichloroketone was established by gas chromatographic analysis, complimented by the mass spectrum of the gc component believed to be the dichloroketone, the mass spectrum of which showed a parent peak at m/e 166 and a fragmentation pattern consistent with 1,1-dichloro-4-methyl-1-penten-3-one.

STEP 2

In Step 2 of this invention, the 1,1-dihalo-4-methyl-1-penten-3-one produced in Step 1 is treated with a selective reagent which reduces the carbonyl function to hydroxyl, while leaving the dihalovinyl group intact.

A number of general techniques are available for the reduction of ketones to alcohols [See for example E. Earl Royals, "Advanced Organic Chemistry," Prentice Hall, Inc., Englewood Cliffs, N.J., 1954, p. 708]. These techniques include the catalyzed addition of hydrogen over a platinum or Raney nickel catalyst, lithium aluminum hydride reductions, and the use of the aluminum alkoxides [the Meerwein-Ponndorf-Verley reduction].

A combination of platinum dioxide and ferrous chloride has been reported to be capable of selectively reducing a carbonyl group in the presence of olefinic unsaturation and halogen [J. Amer. Chem. Soc. 46, 1675 (1924); ibid., 47, 3061 (1925)]. Dichlorovinyl alchohols similar to the product of Step 2 have been prepared by the reduction of other dichlorovinyl ketones [F. Pochat and E. Lewis, Bull. Soc. Chim. Fr., 3846 (1972); L. I. Zakharkin, Izv. Akad. Nauk SSSR., Ser. Khim., 313 (1956)], by the reaction between a Grignard reagent and 3,3-dichloropropenal [L. I. Zakharkin, op. cit.; M. Julia and J. Bullot, Bull. Soc. Chim. Fr. 1828 (1959)], and by treating the corresponding halide with a base [W. Kooyman and W. M. Wagner, Rec. Trav. Chim. Pays-Bas, 77, 923 (1958)].

According to this invention, the reduction of a 1,1-dihalo-4-methyl-1-penten-3-one to the corresponding alcohol is carried out using an aluminum alkoxide in an alcohol.

The procedure is described generally by Wilds [Organic Reactions, II, John Wiley and Sons, Inc., New York, N.Y., 1944, pp. 178–223]. Compared to alternate methods, this procedure gives higher yields, utilizes relatively inexpensive reagents, and is readily adapted to commercial use.

Although several aluminum alkoxide - alcohol combinations have been described in the prior art and could be used, the combination of aluminum isopropoxide and isopropanol is preferred. Aluminum isopropoxide is available in commerce, or it can be prepared in the reaction vessel using the procedure outlined in the reference last cited.

According to the stoichiometry, a 1:1 molar ratio of ketone to aluminum alkoxide is required, but excess aluminum alkoxide is not harmful; if a lesser amount of aluminum alkoxide is used, it is regenerated as it reacts in the presence of the alcohol. Thus, the quantity of aluminum alkoxide is not critical. A 1:1 molar ratio of ketone to aluminum isopropoxide is satisfactory, but it is preferable to employ the latter in about 10% molar excess.

The result of the reaction appears essentially independent of the concentration of the other reactants in the alcohol, and concentrations between about 0.1 and 10 molar, preferably about 1–3 molar, give satisfactory results.

When aluminum isopropoxide-isopropanol is employed, the reaction is carried out conveniently at the reflux temperature of the isopropyl alcohol (82°), the acetone by-product being removed by distillation, preferably continuously as it is produced.

The chemical reaction comprising Step 2 of the process will be understood more readily by reference to Example II.

EXAMPLE II

Preparation of 1,1-Dichloro-3-hydroxy-4-methyl-1-pentene

A. Using Commercial Aluminum Isopropoxide

A mixture of 33.4 gm (0.18 mole) of 1,1-dichloro-4-methyl-1-penten-3-one, 40.9 gm (0.20 mole) of aluminum isopropoxide, and 200 ml of isopropanol was heated at reflux for 2 hours. The by-product, acetone, was distilled periodically from the reaction mixture by alternating between reflux and distillation. When the vapor temperature of the distillate reached 82°, the heating was stopped. To the reaction mixture was then added a cold solution of 70 ml of concentrated hydrochloric acid in 350 ml of water. The aqueous mixture was extracted several times with carbon tetrachloride. The combined extracts were dried over magnesium sulfate and filtered. The carbon tetrachloride was evaporated, and the residue was distilled to give 24.9 gm (82% yield) of 1,1-dichloro-3-hydroxy-4-methyl-1-pentene; b.p., 72°/5mm.

Analysis: Calculated for $C_6H_{10}Cl_2O$: C,42.62; H,5.96; Found: C,42.59; H,5.80. nmr $\delta$ ppm ($CDCl_3$): 0.90(d,3H); 0.95; (d,3H); 2.00–1.33; (m,1H); 2.13; (s,1H); 3.98(dd; 1H), 5.67 (d,1H). ir ($cm^{-1}$): 3330; 1640; 1385; 1366.

B. Including Preparation of Aluminum Isopropoxide

A mixture of 4100 ml of isopropanol and 17.1 gm (0.063 moles) of mercuric chloride was reacted with approximately one half of a 340 gm (12.6 moles) quantity of shredded aluminum foil. After 18 hours the remaining aluminum foil was added to the reaction mixture. The addition of the second portion of aluminum caused an exothermic reaction which necessitated cooling the reaction mixture with large quantities of ice. After the exotherm subsided, the reaction mixture was heated under reflux for 6.25 hours.

The reaction vessel containing the aluminum isopropoxide was fitted with a condenser, and 1737 gm (10.60 moles) of 1,1-dichloro-4-methyl-1-penten-3-one was added. The reaction mixture was heated to reflux, and the evolved acetone was removed by distillation over a 19.25 hour period. The isopropanol was then removed by distillation, and the residue was separated into two portions of 1100 ml and 1900 ml respectively. The 1100 ml portion was hydrolyzed in 3000 ml of aqueous hydrochloric acid and then washed three times with 900 ml of benzene. For the 1900 ml portion, 5100 ml of aqueous hydrochloric acid and 1500 ml of benzene were used. The benzene washes were combined and washed with 4000 ml of water. The organic layer was separated and dried over magnesium sulfate. Most of the benzene was removed by distillation under atmospheric pressure. The residue was filtered, and the last trace of solvent was removed by distillation under reduced pressure. The residue was distilled under reduced pressure to give 1698 gm (94.8% yield) of 1,1-dichloro-3-hydroxy-4-methyl-1-pentene; b.p., 67°–83°/4–7mm.

STEP 3

In Step 3 of this invention, the 1,1-dihalo-3-hydroxy-4-methyl-1-pentene produced in Step 2 is dehydrated to yield the desired 1,1-dihalo-4-methyl-1,3-pentadiene.

The dehydration of an alcohol to produce an olefin is a well known chemical reaction [E. Earl Royals, op. cit., p. 230]. A number of different techniques may be employed to effect the dehydration. These include, for example, the use of acids such as sulfuric acid, phosphoric acid, oxalic acid, paratoluene sulfonic acid, and the like; pyrolysis over metal oxides such as aluminium oxide, thorium oxide, silicas, and silicates; and treatment with phosphorus pentoxide, potassium bisulfate, potassium pyrosulfate, and the like.

The dehydration of alcohols to olefins does not proceed without difficulty, however; the formation of ethers is a troublesome side reaction, especially when acid dehydrating agents are used. Other side reactions are also possible in the case of an unsaturated alcohol such as a 1,1-dihalo-3-hydroxy-4-methyl-1-pentene, which is subject to polymerization leading to intractable oils and tars. Most of the metal oxide catalysts are only effective at temperatures of 200° or higher, temperatures which sensitive compounds will not withstand.

Whereas the dehydration of Step 3 can be effected by the techniques of the prior art, a novel process of general applicability has now been discovered by which the dehydration of a 1,1-dihalo-3-hydroxy-4-methyl-1-pentene may be carried out catalytically at a relatively low temperature to produce a 1,1-dihalo-4-methyl-1,3-pentadiene with a minimum of impurities. This preferred method of dehydration employs an activated clay absorbent as the catalyst.

The clay may be suspended in the neat alcohol, or in a solvent such as heptane, toluene, or xylene and the like. The preferred solvents have boiling points of at least about 100°, or form azeotropic mixtures with water.

The clay is used in catalytic amounts, in the range of about 0.1–5%, preferably about 2%, by weight with respect to the alcohol. The dehydration is effected at temperatures of 100°–200°, preferably between about 110° and 120°.

Step 3 of this process will be more fully understood by reference to Example III.

EXAMPLE III

Preparation of 1,1-Dichloro-4-methyl-1,3-pentadiene

A. Using Potassium Bisulfate

A mixture of 10.1 gm (0.059 mole) of 1,1-dichloro-3-hydroxy-4-methyl-1-pentene and 1.0 gm of potassium bisulfate was heated slowly from 100° to 150°. The mixture was held at 150° for 0.5 hour, and then allowed to cool. Water and benzene were added. The benzene layer was separated, dried over magnesium sulfate, and then filtered. Gas chromatographic analysis of the filtrate indicated a 14% conversion to 1,1-dichloro-4-methyl-1,3-pentadiene.

B. Using an Activated Clay Absorbent

1. Employing Toluene as a Solvent

A mixture of 33.8 gm (0.20 mole) of 1,1-dichloro-3-hydroxy-4-methyl-1-pentene and 0.5 gm of an activated clay absorbent in 26 ml of toluene was heated at 105°–127° for 2.5 hours in a vessel fitted with a condenser and a Dean-Stark trap. During this time, 3.6 ml (0.20 mole) of water was collected in the trap. The toluene was removed by distillation, and the residue was distilled to give 25.2 gm (83.4% yield) of 1,1-dichloro-4-methyl-1,3-pentadiene.

A suitable activated clay absorbent is characterized typically by requiring about 8 mg KOH/gm of clay to neutralize the acid contained therein, having a surface area of about 275 m$^2$/gm, and a particle size smaller than about 100 mesh. Satisfactory clays may be found among the Filtrol ® activated clay absorbents produced by the Filtrol Corporation, 5959 West Century Boulevard, Los Angeles, California 90045.

2. In the Absence of a Solvent

In a reaction vessel fitted with a condenser was placed 6.8 gm (0.0402 moles) of 1,1-dichloro-3-hydroxy-4-methyl-1-pentene and 0.2 gm of the activated clay absorbent of Example III B 1. The stirred mixture was swept with nitrogen while being heated rapidly to 110°, and then for 1 hour as the temperature was raised from 110° to 135°. Gas chromatographic analysis then indicated the reaction mixture to be 96% 1,1-dichloro-4-methyl-1,3-pentadiene. The mixture was distilled under reduced pressure to give 6.3 gm (89% yield) of crude 1,1-dichloro-4-methyl-1,3-pentadiene.

C. Using Phosphoric Acid

To 32.4 gm (0.192 mole) of 1,1-dichloro-3-hydroxy-4-methyl-1-pentene, purged with nitrogen, was added 0.25 gm of concentrated phosphoric acid. The reaction mixture was heated for 3.25 hours at 145°–157°. Then an additional 0.1 gm of concentrated phosphoric acid was added. Heating at 157°–159° was continued for 2 hours.

During the reaction, 3.4 ml (theory 3.5 ml) of water and 2.5 ml of oil were collected by distillation. Gas chromatographic analysis of the oil indicated it to be 56% 1,1-dichloro-4-methyl-1,3-pentadiene. The distillate and the cooled reaction mixture were combined with 20 ml of carbon tetrachloride, and the combination was washed with 10 ml each of water, dilute aqueous sodium bicarbonate, then with two portions of water. The organic layer was dried over magnesium sulfate and filtered. The carbon tetrachloride was removed by distillation at atmospheric pressure. The residue was distilled under reduced pressure to give, in the major fraction, 19.6 gm of crude 1,1-dichloro-4-methyl-1,3-pentadiene.

D. Using Potassium Pyrosulfate

1. In the Absence of a Solvent

A stirred mixture of 9.0 gm (0.053 moles) of 1,1-dichloro-3-hydroxy-4-methyl-1-pentene and 0.45 gm of potassium pyrosulfate, purged with nitrogen, was heated at 125°–135° for 2.5 hours, then at 140°–145° for 1.5 hours. The reaction mixture was allowed to cool over 16 hours. Gas chromatographic analysis of the reaction mixture indicated that it contained 1,1-dichloro-4-methyl-1,3-pentadiene.

2. Employing a Solvent

In a reaction vessel containing a Dean-Stark trap were placed 8.6 gm (0.051 moles) of 1,1-dichloro-3-hydroxy-4-methyl-1-pentene and 0.5 gm of potassium pyrosulfate in 50 ml of toluene. The stirred mixture was heated under reflux for 1.75 hours. No reaction occurred, judging by the absence of water in the Dean-Stark trap. The toluene in the reaction mixture was removed by distillation and replaced by 50 ml of xylene. The mixture was heated under reflux for 2 hours. A trace of water collected in the Dean-Stark trap during this period. Gas chromatographic analysis of the reaction mixture indicated it to be 10% reaction product and 90% starting alcohol. Heating under reflux was continued for another 9 hours, at the end of which gas chromatographic analysis indicated that the reaction mixture contained 53% 1,1-dichloro-4-methyl-1,3-pentadiene and 47% starting material.

I claim:

1. A process for preparing 1,1-dichloro-4-methyl-1,3-pentadiene which comprises:
   (a) condensing vinylidene chloride with isobutyryl chloride in the presence of a Lewis acid to produce 1,1-dichloro-4-methyl-1-penten-3-one,
   and then
   (b) reducing said 1,1-dichloro-4-methyl-1-penten-3-one with aluminum isopropoxide and isopropanol to produce 1,1-dichloro-3-hydroxy-4-methyl-1-pentene,
   and then
   (c) dehydrating said 1,1-dichloro-3-hydroxy-4-methyl-1-pentene at a temperature between about 100° C and 200° C with an activated clay absorbent, said clay requiring about 8 mg KOH/gm of clay to neutralize the acid contained therein, having a surface area of about 275 m$^2$/gm, and a particle size smaller than about 100 mesh, to produce said 1,1-dichloro-4-methyl-1,3-pentadiene.

2. A process for preparing 1,1-dichloro-4-methyl-1,3-pentadiene which comprises:
   (a) reducing 1,1-dichloro-4-methyl-1-penten-3-one with aluminum isopropoxide and isopropanol to produce 1,1-dichloro-3-hydroxy-4-methyl-1-pentene,
   and then
   (b) dehydrating said 1,1-dichloro-3-hydroxy-4-methyl-1-pentene at a temperature between about 100° C and 200° C with an activated clay absorbent, said clay requiring about 8 mg KOH/gm of clay to neutralize the acid contained therein, having a surface area of about 275 m$^2$/gm, and a particle size smaller than about 100 mesh, to produce said 1,1-dichloro-4-methyl-1,3-pentadiene.

3. A process for preparing 1,1-dichloro-4-methyl-1,3-pentadiene which comprises dehydrating 1,1-dichloro-3-hydroxy-4-methyl-1-pentene at a temperature between about 100° C and 200° C with an activated clay absorbent, said clay requiring about 8 mg KOH/gm of clay to neutralize the acid contained therein, having a surface area of about 275 m$^2$/gm, and a particle size smaller than about 100 mesh, to produce said 1,1-dichloro-4-methyl-1,3-pentadiene.

* * * * *